United States Patent
Ramazanian et al.

(10) Patent No.: US 9,757,267 B1
(45) Date of Patent: Sep. 12, 2017

(54) FOREARM AND WRIST FRACTURE TABLE

(71) Applicants: Taghi Ramazanian, Falls Church, VA (US); Mohammad Gharehbeglou, Tehran (IR); Safa Hoodeshenas, Falls Church, VA (US)

(72) Inventors: Taghi Ramazanian, Falls Church, VA (US); Mohammad Gharehbeglou, Tehran (IR); Safa Hoodeshenas, Falls Church, VA (US)

( * ) Notice: Subject to any disclaimer, the term of this patent is extended or adjusted under 35 U.S.C. 154(b) by 0 days.

(21) Appl. No.: 15/291,035

(22) Filed: Oct. 11, 2016

(51) Int. Cl.
*A61F 5/042* (2006.01)
*A61H 1/02* (2006.01)
*A61B 17/60* (2006.01)

(52) U.S. Cl.
CPC .............. *A61F 5/042* (2013.01); *A61B 17/60* (2013.01); *A61H 1/0222* (2013.01); *A61H 1/0285* (2013.01)

(58) Field of Classification Search
CPC .. A61F 5/04; A61F 5/042; A61F 5/048; A61F 5/05841; A61F 5/05858; A61F 5/05866; A61F 5/05875; A61F 5/058; A61F 5/0102; A61F 5/013; A61F 5/0104; A61H 1/0218; A61H 1/0274; A61H 1/0285; A61H 1/0288; A61H 1/0222; A61H 2205/06; A61H 2205/065; A61H 2205/067; A61H 2205/062; A61H 1/02; A61H 1/02177; A61H 2001/1253; A61H 2001/1269; A61H 2001/1276; A61H 2001/1638; A61H 2001/1664; A61H 2203/04; A61H 2203/0425; A61H 2203/0431; A61H 1/0277; A61H 2201/1253; A61H 2201/1269; A61H 2201/1276; A61H 2201/1638; A61H 2201/1664; Y10T 403/32311; Y10T 403/32319;
(Continued)

(56) References Cited

U.S. PATENT DOCUMENTS 2,584,203 A * 2/1952 Hart .................... A61F 5/04
24/129 D
3,693,617 A 9/1972 Trott
(Continued)

FOREIGN PATENT DOCUMENTS

WO 2005/027749 3/2005

*Primary Examiner* — Kari Rodriguez
*Assistant Examiner* — Camtu Nguyen
(74) *Attorney, Agent, or Firm* — Falati Law Firm

(57) ABSTRACT

A forearm and wrist fracture table includes base members, vertical bars, horizontal bars, an elbow support member and a hand support member. The vertical bars includes a first vertical bar and a second vertical bar attached to the support base members. The horizontal bars are attached between the support base members and vertical bars to provide horizontal stability and length adjustment between the support base members and the vertical bars. The elbow support member is attached to the first vertical bar to provide support for the elbow. The hand support member is attached to the second vertical bar to receive and support a hand extending from the elbow, wherein the fractured arm is supported between the elbow support member and the hand support member, wherein a surgeon is allowed to modulate an amount of needing pressure required to distract fracture fragments, and thereby reducing fracture and healing the fracture site.

4 Claims, 6 Drawing Sheets

(58) Field of Classification Search
CPC .......... Y10T 403/32639; A47C 20/203; A47C 20/023; A61B 17/60
USPC ....... 128/845; 602/32–33, 35–36, 39; 5/623, 5/650, 658
See application file for complete search history.

(56) References Cited

U.S. PATENT DOCUMENTS

| | | | |
|---|---|---|---|
| 3,745,996 A | | 7/1973 | Rush, Sr. |
| 4,653,482 A | * | 3/1987 | Kurland ................ A61G 13/12 5/601 |
| 5,074,291 A | * | 12/1991 | Carter .................. A61G 13/12 5/646 |
| 5,472,407 A | * | 12/1995 | Schenck ............. A61H 1/0288 601/40 |
| 5,735,806 A | * | 4/1998 | Leibovic .................. A61F 5/04 128/878 |
| 6,533,743 B1 | * | 3/2003 | Moss ....................... A61F 5/04 602/32 |
| 6,895,969 B2 | * | 5/2005 | Malcolm .................. A61F 5/04 128/845 |
| 7,143,458 B2 | * | 12/2006 | Slater, Jr. .............. A61F 5/3769 128/845 |
| 8,721,641 B2 | | 5/2014 | Ottoboni et al. |
| 8,870,803 B2 | | 10/2014 | Reiley et al. |
| 2006/0200061 A1 | * | 9/2006 | Warkentine ............... A61F 5/04 602/32 |

* cited by examiner

FOREARM AND WRIST FRACTURE TABLE

BACKGROUND

The present invention relates to an external support device, which is designed to assist in the corrective treatment of bone fractures.

Bone fractures are typically treated by restoring the fractured pieces of bone to their natural positions and maintaining those positions while the bone heals. Briefly, the fractured bone(s) is aligned in good position (also called reduction) and then immobilized with a cast that holds the bones in position and immobilizes the joints above and below the fracture. When the initial post-fracture edema or swelling goes down, the fracture may be placed in a removable brace or orthosis. In cases of complex or open fractures, surgical nails, screws, plates and wires may be used to internally hold the fractured bone together.

The surgical implantation of these internal fixation devices, however, may cause extensive trauma to the patient, increase potential for infection, and require second surgery for their removal. An alternative to internal fixation devices is the external fixation device. Pins or screws are placed into the broken bone above and below the fracture site to reposition and immobilize the bone fragments. The pins or screws are connected to a metal bar or bars outside the skin to form a stabilizing frame that holds the bones in the proper position so they can heal. After an appropriate period of time, the external fixation device is removed.

Orthopedic surgeons generally try to reduce bone fractures in patients under general or local anesthesia to relieve pain and muscle spasm, but because of the compression or overriding of the fracture fragments, it is at times necessary to disengage the fracture fragments as a first step of the reducing process. Therefore, in order to achieve this, orthopedic surgeons can put a longitudinal traction on the upper limb while a colleague holds the patient's arm at a certain degree of flexion, for example, at a ninety-degree flexion of the elbow. This traction disengages the fracture fragments and at this moment the surgeon can attempt to reduce the fracture by gently manipulating the fracture fragments. After this step, the upper limb is immobilized by putting a long arm cast, which is meant to cover the whole upper limb while the elbow is positioned at ninety degrees. The upper arm cast also allows the patient to move all digits freely thus preventing finger stiffness.

In situations where the fracture site is too swollen to put a cast on it; the case is not used in such situations because it would pose a great risk due to the potential for blocking of the blood supply to the forearm and hand. In this situation, the surgeon may decide to use a splint in order to immobilize the arm and wait till the swelling reduces and the limb is ready for casting. After casting, the patient is encouraged to elevate his/her arm to prevent further swelling and continuous active movement of fingers and shoulder joint to prevent stiffness in these joints.

After reduction of the fracture, the orthopedic surgeon orders an x-ray to evaluate fracture reduction because of the risk of displacement due to the decrease in swelling and due to the loss of the cast fitness and collapsing the fracture fragments. This process of obtaining x-rays is typically repeated several times over a period of about one month. Any unacceptable displacement will be reduced again. After three weeks, the chance of fracture fragment displacement is low and after six weeks the surgeon would remove the cast. For non-displaced fractures, immobilization time is even shorter and the cast can be removed after three weeks.

In the above mentioned medical procedures, there is a lack of an adjustable device which can provide proper stabilization of the upper arm, so that the surgeon can work on the fracture fragments as well as perform x-ray on the fracture site in a steady and stable manner.

Hence, there is a long felt but unresolved need in the orthopedic medical community for a fractured arm support device, namely a forearm and wrist fracture table, which can stabilize and fix the upper limb, and at the same time allow the surgeon to distract the fracture fragments in a gradual and gentle manner to reduce the fracture. Further, there is a need in the art for a forearm and wrist fracture table that makes it comfortable for the surgeon to perform x-rays simultaneously to inserting per cutaneous pins into fracture sites to establish better fixation.

SUMMARY OF THE INVENTION

This summary is provided to introduce a selection of concepts in a simplified form that are further disclosed in the detailed description of the disclosure. This summary is not intended to identify key or essential inventive concepts of the claimed subject matter, nor is it intended for determining the scope of the claimed subject matter.

The forearm and wrist fracture table disclosed herein addresses the above mentioned need for a device which can stabilize and fix upper limb, and at the same time gives the surgeon a possibility to distract the fracture fragments in a gradual and very gentle manner to reduce the fracture easily. The forearm and wrist fracture table is configured to support a fractured arm of a patient during a medical procedure to rectify a fracture site of the fractured arm. The forearm and wrist fracture table comprises a set of support base members, a set of vertical bars, a set of horizontal bars, an elbow support member, and a hand support member. The vertical bars comprising a first vertical bar and a second vertical bar removably attached on an upper surface of each of the support base members.

One aspect of the present disclosure is directed to a forearm and wrist fracture table configured to support a fractured arm of a patient during a medical procedure in order to rectify a fracture site of the fractured arm, comprising a set of support base members; a set of vertical bars comprising a first vertical bar and a second vertical bar removably attached on upper surfaces of each of the support base members; a set of horizontal bars removably attached between the support base members and the vertical bars, wherein the horizontal bars are configured to provide horizontal stability and length adjustment between the support base members and the vertical bars according to the size of the fractured arm; an elbow support member defined by a cylindrical member removably attached on an upper section of the first vertical bar, wherein the elbow support member provides support for the elbow of the fractured arm; a hand support member defined by a curved plate member removably attached to an upper section of the second vertical bar, wherein the hand support member is configured to receive and support a hand extending from the elbow of the patient, wherein the fractured arm is supported between the elbow support member and the hand support member, and further wherein the support device allows for the needing pressure to be modulated and adjusted as required to distract fracture fragments, and thereby reduce and heal the fracture site.

In one embodiment, the set of support base members comprising leg members are fixedly attached proximal to opposing ends of a rod member, and wherein the leg members are configured to contact the ground surface, thereby providing support. In another embodiment, the leg members are defined by a screw jack assembly where a lead screw is adjusted via a gripper wheel which changes the height of the support base members from the ground level. In one embodiment, each of the vertical bars comprises concentric rectangular pipes sliding over each other, wherein a plurality of holes are positioned on an inner pipe, and a hole positioned on an outer pipe through which a pin is introduced which selectively adjusts the length of the vertical bars. In another embodiment, each of the horizontal bars comprises concentric rectangular pipes sliding over each other, wherein a plurality of holes are positioned on an inner pipe, and a hole positioned on an outer pipe through which a pin is introduced which selectively adjusts the length of the horizontal bars.

In one embodiment, the elbow support member is defined by the cylindrical member and is positioned above a plate section. In another embodiment, the hand support member comprises the curved plate member fixedly attached at the distal end of a rod member which is threadably adjusted via a fastening wheel positioned at the opposing end of the rod member, wherein the fastening wheel adjusts the length of the curved plate member according to the length of the fractured arm. In one embodiment, the support device is portable, and wherein the support base members, the vertical bars, the horizontal bars, the elbow support member, and the hand support member are configured to be carried separately, and easily and quickly assembled near the patient with the fractured arm when the patient is unable to move.

In one embodiment, the arm support device is configured to allow the operator to perform a cutaneous pinning technique on the fractured arm, and further wherein the arm support device is configured to allow for the evaluation of the fractured site by permitting the simultaneous capture of x-rays of the arm and the adjusting of the amount of needing pressure required to distract fracture fragments.

In one embodiment, the arm support device is capable of traction and reduction maneuvers on the fracture site, thereby reducing the fracture. In another embodiment, the arm support device is configured to allow surgeons to perform intraoperative imaging of wrist and forearm fractures, and pinning of the fractured site under fluoroscopy for wrist and forearm fractures. In one embodiment, the arm support device is configured to enhance the surgeon's control on operation position during pinning, and thereby shorten duration of surgery. In one embodiment, the forearm and wrist fracture table is a fractured arm support device.

Another aspect of the present disclosure is directed to a forearm and wrist fracture table made of one or a combination of plastic and metal, configured to support a fractured arm of a patient during a medical procedure to rectify a fracture site of the fractured arm, comprising: a set of support base members, wherein the set of support base members comprise leg members fixedly attached proximal to opposing ends of a rod member; a set of vertical bars comprising a first vertical bar and a second vertical bar removably attached on upper surfaces of each of the support base members; a set of horizontal bars removably attached between the support base members and the vertical bars, wherein the horizontal bars are configured to provide horizontal stability and length adjustment between the support base members and the vertical bars according to the size of the fractured arm; an elbow support member defined by a cylindrical member removably attached on an upper section of the first vertical bar, wherein the elbow support member is positioned above a plate section to provide support for the elbow of the fractured arm; a hand support member defined by a curved plate member removably attached to an upper section of the second vertical bar, wherein the hand support member comprises the curved plate member fixedly attached at the distal end of a rod member which is adjusted via a fastening wheel positioned at the opposing end of the rod member, wherein the hand support member is configured to receive and support a hand extending from the elbow of the patient, wherein the fractured arm is supported between the elbow support member and the hand support member, wherein the arm support device is configured to allow the operator to adjust the amount of needing pressure required to distract fracture fragments, thereby causing a reduction and promoting healing of the fracture site, and wherein the device is configured to allow this adjusting of the needing pressure to be done simultaneously to performing a cutaneous pinning technique on the fractured arm and the concurrent evaluation of the fractured site via x-ray, and further wherein the arm support device is capable of traction and reduction maneuvers on the fracture site, thereby reducing the fracture.

In one embodiment, the leg members are configured to contact the ground surface to provide support for the forearm and wrist fracture table. In another embodiment, the fingers of the hand of a patient are secured to the curved plate member by fastening the fingers to the curved plate member using a strap member which is configured to be looped through openings positioned on the curved plate member, wherein the strap member is looped through the openings and between gaps of the fingers. In one embodiment, the horizontal bars are adjusted to change the distance between the elbow support member and the hand support member to facilitate a coarse tuning, wherein the traction generated by the coarse tuning allows the surgeon to maintain longitudinal alignment of the fracture site and evaluate the fracture under fluoroscopy.

In one embodiment, the fastening wheel adjusts the length of the curved plate member according to the length of the fractured arm. In a related embodiment, the fastening wheel further comprises a handle configured to rotate the fastening wheel, thereby allowing for the fine tuning with the fastening wheel to adjust the fracture site, wherein a clockwise turning of the handle increases the traction in the fracture site, and counter-clock turning of the handle relaxes traction in the fracture site.

Another aspect of the present disclosure is directed to a method for supporting a fractured arm of a patient, comprising: (a) providing a portable forearm and wrist fracture table comprising: a set of support base members; a set of vertical bars comprising a first vertical bar and a second vertical bar removably attached on upper surfaces of each of the support base members; a set of horizontal bars removably attached between the support base members and the vertical bars, wherein the horizontal bars are configured to provide horizontal stability; an elbow support member defined by a cylindrical member removably attached on an upper section of the first vertical bar; and a hand support member defined by a curved plate member removably attached to an upper section of the second vertical bar; (b) assembling the support base members, the vertical bars, the horizontal bars, the elbow support member, and the hand support member near the patient with the fractured arm; (c) adjusting the horizontal bars to change the length between the support base members and the vertical bars according to the size of the fractured arm; (d) positioning the elbow of a patient on the elbow support member, wherein the elbow support member provides support for the elbow of the fractured arm; (e) receiving and supporting a hand extending from the elbow of the patient via the hand support member, wherein the fractured arm is supported between the elbow support member and the hand support member; (f) allowing a surgeon to modulate an amount of needing pressure required to distract fracture fragments, and thereby reducing and healing the fracture site; (g) simultaneously performing a cutaneous pinning technique on the fractured arm, and evaluating the fractured site via x-ray simultaneously during modulation of the amount of needing pressure required to distract fracture fragments; and (h) allowing the surgeon to perform traction and reduction maneuver on the fracture site, thereby reducing the fracture.

In one embodiment of the presently taught method, the method further comprises performing intraoperative imaging of wrist and forearm fractures, and pinning of the fractured site under fluoroscopy for wrist and/or forearm fractures.

In one embodiment, the fractured arm is supported between the elbow support member and the hand support member, where a surgeon is allowed to modulate an amount of needing pressure required to distract fracture fragments, and thereby reducing fracture and healing the fractured site. In another embodiment, the forearm and wrist fracture table further allows the surgeon to perform a cutaneous pinning technique on the fractured arm, and evaluating the fractured site via x-ray simultaneously during modulation of the amount of pressure required to distract fracture fragments. In an embodiment, the forearm and wrist fracture table further allows the surgeon to perform traction and reduction maneuver on the fracture site, thereby reducing the fracture.

In an embodiment, the forearm and wrist fracture table is configured to shorten surgery duration, and enhance the surgeon's control on operation position during pinning. In an embodiment, the forearm and wrist fracture table is configured to allow variable tensile force to be applied on fractured limbs during reduction and fixation. In an embodiment, the forearm and wrist fracture table is portable, where the support base members, the vertical bars, the horizontal bars, the elbow support member, and the hand support member are configured to be carried separately and assembled near the patient with the fractured arm when the patient is unable to move.

Another aspect of the present disclosure is directed to a method for supporting a fractured arm of a patient. A portable forearm and wrist fracture table comprising a set of support base members, a set of vertical bars, a set of horizontal bars, an elbow support member, and a hand support member is provided. The vertical bars comprise a first vertical bar and a second vertical bar removably attached on upper surfaces of each of the support base members, and the horizontal bars are removably attached between the support base members and the vertical bars, where the horizontal bars are configured to provide horizontal stability. The elbow support member is defined by a cylindrical member removably attached on an upper section of the first vertical bar, and the hand support member is defined by a curved plate member removably attached to an upper section of the second vertical bar.

A surgeon or a user assembles the support base members, the vertical bars, the horizontal bars, the elbow support member, and the hand support member near the patient with the fractured arm, and adjusts the horizontal bars to change the length between the support base members and the vertical bars according to the size of the fractured arm. Then the surgeon positions the elbow of a patient on the elbow support member, where the elbow support member provides support for the elbow of the fractured arm. The hand support member receives and supports a hand extending from the elbow of the patient via the hand support member, where the fractured arm is supported between the elbow support member and the hand support member.

In one embodiment, the forearm and wrist fracture table allows a surgeon to modulate an amount of needing pressure required to distract fracture fragments which reduces and heals the fracture site, and simultaneously allows the surgeon to 1) perform a cutaneous pinning technique on the fractured arm, and 2) evaluate the fractured site via x-ray when modulating the amount of needing pressure required to distract fracture fragments. This allows the surgeon to perform traction and reduction maneuvers on the fracture site, thereby reducing the fracture. In addition, the fastening wheel further comprises a handle configured to rotate the fastening wheel and fine tune the fastening wheel to adjust the fracture site.

One aspect of the present disclosure is directed to a forearm and wrist fracture table, comprising: a set of support base members, wherein the set of support base members comprise leg members fixedly attached proximal to opposing ends of a rod member; a set of vertical bars comprising a first vertical bar and a second vertical bar removably attached on upper surfaces of each of the support base members; a set of horizontal bars removably attached between the support base members and the vertical bars, wherein the horizontal bars are configured to provide horizontal stability and length adjustment between the support base members and the vertical bars according to the size of the fractured arm; an elbow support member defined by a cylindrical member removably attached on an upper section of the first vertical bar, wherein the elbow support member is positioned above a plate section to provide support for the elbow of the fractured arm; a hand support member defined by a curved plate member removably attached to an upper section of the second vertical bar, wherein the hand support member comprises the curved plate member fixedly attached at the distal end of a rod member which is adjusted via a fastening wheel positioned at the opposing end of the rod member, wherein the hand support member is configured to receive and support a hand extending from the elbow of the patient, wherein the fractured arm is supported between the elbow support member and the hand support member, wherein the arm support device is configured to allow the operator to adjust the amount of needing pressure required to distract fracture fragments, thereby causing a reduction and promoting healing of the fracture site, and wherein the device is configured to allow this adjusting of the needing pressure to be done simultaneously to performing a cutaneous pinning technique on the fractured arm, wherein the arm support device is capable of traction and reduction maneuvers on the fracture site, and wherein the fastening wheel further comprises a handle configured to rotate the fastening wheel to allow for the fine tuning with the fastening wheel to adjust the length of the curved plate member according to the length of the fractured arm, wherein a clockwise turning of the handle increases the traction in the fracture site, and counter-clock turning of the handle relaxes traction in the fracture site.

In one embodiment, each of the vertical bars comprises concentric rectangular pipes sliding over each other, wherein a plurality of holes are positioned on an inner pipe, and a hole positioned on an outer pipe through which a pin is introduced which selectively adjusts the length of the vertical bars; and wherein each of the horizontal bars comprises concentric rectangular pipes sliding over each other, wherein a plurality of holes are positioned on an inner pipe, and a hole positioned on an outer pipe through which a pin is introduced which selectively adjusts the length of the horizontal bars.

In an embodiment, the forearm and wrist fracture table further comprises another hand support member configured to position the fractured arm of the patient during per cutaneous pin fixation to treat distal radius fracture of the fractured arm, where the hand support member comprises a rotatable sphere pivotally disposed within a spherical shell. A portion of the rotatable sphere is configured to fixedly attach a hand holding rib, where the patient is allowed to position the fractured arm over any hand support device fastened over the hand holding rib to perform one or combination of wrist flexion and ulnar deviation.

In an embodiment, the forearm and wrist fracture table disclosed here further comprises a first hemi-spherical shell and a second hemi-spherical shell which are fastened to each other to define the spherical shell. The hand support member also comprises a generally cube shaped support base member positioned on the rotatable sphere to fasten and support the hand holding rib. The hand holding rib comprises an assembly of four flanged plates radially positioned with respect to each other, where each radially flanged plate comprises fastener receiving holes to receive and fasten one or more types of hand support devices.

BRIEF DESCRIPTION OF THE DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific methods and components disclosed herein.

DETAILED DESCRIPTION

The present disclosure generally relates to the field of devices for fracture reduction and fracture repair and more specifically relates to a device for supporting a fractured arm during fracture reduction surgery and fluoroscopy imaging.

Figure 1:
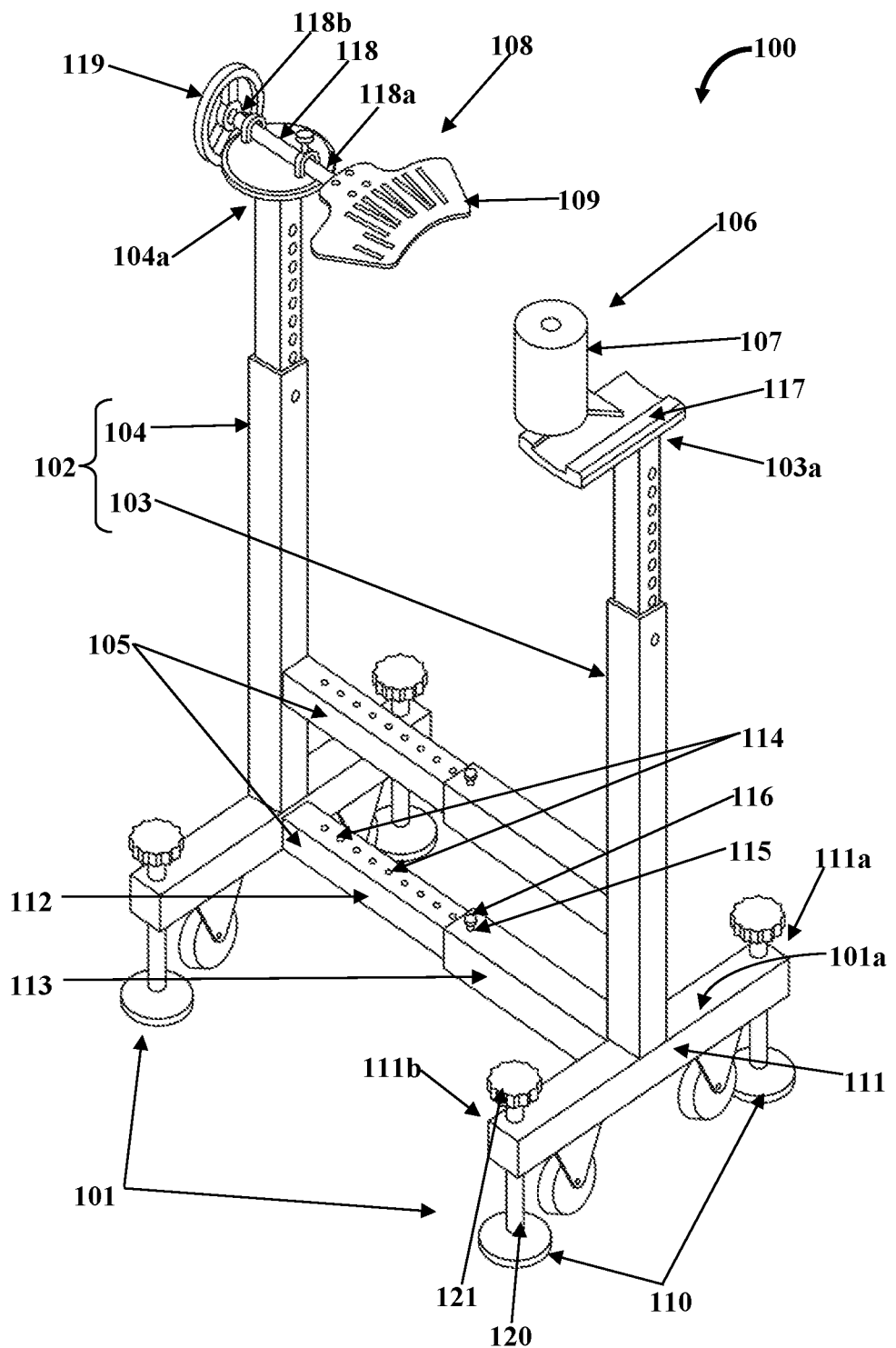
FIG. 1 exemplarily illustrates a front perspective view of a forearm and wrist fracture table.

FIG. 1 exemplarily illustrates a front perspective view of a forearm and wrist fracture table 100. The forearm and wrist fracture table 100 is configured to support a fractured arm 300 of a patient during a medical procedure to rectify a fractured site of the fractured arm 300. The forearm and wrist fracture table 100 comprises a set of support base members 101, a set of vertical bars 102, a set of horizontal bars 105, an elbow support member 106, and a hand support member 108. The vertical bars 102 comprises a first vertical bar 103 and a second vertical bar 104, removably attached on upper surfaces 101a of each of the support base members 101. The horizontal bars 105 are removably attached between the support base members 101 and the vertical bars 102, wherein the horizontal bars 105 are configured to provide horizontal stability and length adjustment between the support base members 101 and the vertical bars 102 according to the size of the fractured arm 300.

The elbow support member 106 is defined by a cylindrical member 107 removably attached on an upper section 103a of the first vertical bar 103, wherein the elbow support member 106 provides support for the elbow of the fractured arm 300. The hand support member 108 is defined by a curved plate member 109 removably attached to an upper section 104a of the second vertical bar 104, wherein the hand support member 108 is configured to receive and support a hand extending from the elbow of the patient, wherein the fractured arm 300 is supported between the elbow support member 106 and the hand support member 108. The surgeon is allowed to modulate the needing pressure required to distract fracture fragments, thereby reducing and healing the fracture site.

The forearm and wrist fracture table 100 further allows the surgeon to perform a cutaneous pinning technique on the fractured arm 300, and enables him/her to evaluate the fractured site via x-ray while simultaneously modulating the pressure required to distract the fracture fragments. The forearm and wrist fracture table 100 further allows the surgeon to perform traction and reduction maneuver on the fracture site, thereby reducing the fracture. The forearm and wrist fracture table 100 can be made of, for example, one or a combination of plastic and metal. The set of support base members 101 may comprise leg members 110 fixedly attached proximal to opposing ends 111a and 111b of a rod member 111, wherein the leg members 110 are configured to contact ground surface, thereby providing support.

The leg members 110 may be defined by a screw jack assembly 120 and 121 where a lead screw 120 is adjusted via a gripper wheel 121 which changes the height of the support base members 101 from the ground surface or ground level.

Each of the horizontal bars 105 may comprise concentric rectangular pipes 112 and 113 sliding over each other, where multiple holes 114 are positioned on an inner pipe 112, and a hole 115 positioned on an outer pipe 113 through which a pin 116 is introduced which selectively adjusts the length of the horizontal bars 105, similarly as shown in FIG. 1. In one example, each of the vertical bars 102 comprise concentric rectangular pipes sliding over each other, wherein multiple holes are positioned on an inner pipe, and a single hole is positioned on an outer pipe through which a pin is introduced which selectively adjusts the length of the vertical bars 102. The elbow support member 106 defined by the cylindrical member 107 is positioned above a plate section 117. The hand support member 108 comprises the curved plate member 109 fixedly attached at the distal end 118a of a rod member 118 which is threadably adjusted via a fastening wheel 119 positioned at the opposing end 118b of the rod member 111, wherein the fastening wheel 119 adjusts the length of the curved plate member 109 according to the length of the fractured arm 300.

The forearm and wrist fracture table 100 can be portable, wherein the support base members 101, the vertical bars 102, the horizontal bars 105, the elbow support member 106, and the hand support member 108 are configured to be carried separately and assembled in any hospital to treat the patient with the fractured arm. In such cases, the patient's fractured arm is allowed to be positioned in a way where further movement of the fractured site is restricted.

The forearm and wrist fracture table 100 can provide support to the fractured arm of the patient before being transported to a nearby medical facility. The portable configuration of the forearm and wrist fracture table 100 can enable a user or a surgeon to carry the forearm and wrist fracture table 100 to a hospital near the location of the patient, where the patient suffered the fractured arm. In such a scenario, the forearm and wrist fracture table 100 is thus assembled in a nearby hospital so that immediate medical attention can be given to the patient. Therefore, not only does the forearm and wrist fracture table 100 provide assistance and support during surgical procedures of a fractured arm, but its portable nature also provides support under urgent conditions and/or in situations where a patient has suffered a fractured arm, is close to a small hospital in a remote location and is unable to move.

In current routine methods, which are generally performed under general anesthesia or regional block to relieve pain and muscle spasm along a fracture site, the orthopedic surgeon tries to reduce the fracture via conventional methods. Because of the compression or overriding of the fracture fragments, it is necessary to disengage the fracture fragments as a first step of the reduction process. Then the orthopedic surgeon positions longitudinal traction on the upper limb while his/her assistant will be holding the patient's arm at ninety degree flexion of elbow. This traction disengages the fracture fragments and at this moment surgeon tries to reduce fracture by gentle manipulation of the fracture fragments.

After this step, the upper arm is immobilized by positioning a long arm cast which is configured to cover the whole upper limb while the elbow is positioned in ninety degrees angle. The upper arm cast allows the patient to move all digits freely to prevent finger stiffness. This forearm and wrist fracture table 100 helps the medical personnel to stabilize and fix the upper limb and at the same time gives the surgeon a possibility to distract the fracture fragments in a gradual and very gentle manner in order to reduce the fracture easily. Further, the forearm and wrist fracture table 100 enables the surgeon to take x-ray and insert per cutaneous pins into fracture sites to establish better fixation, and therefore the height and length of the fracture table is easily adjustable based on the patient physique.

The forearm and wrist fracture table 100, also referred to as the wrist-forearm fracture reduction-fixation apparatus, facilitates wrist-forearm fracture reduction-fixation with mechanical connections comprising several metal and plastic rods and special biomedical engineering design for patients with upper extremity fractures in the upper arms, especially those with forearm and wrist fractures. The forearm and wrist fracture table 100 is manufactured by connecting metal and plastic parts based on a precise biomedical engineering process in compliance with surgical criteria on correct position, reduction and pinning wrists and forearms.

In one example, the forearm and wrist fracture table 100 allows surgeons to perform intraoperative imaging of wrist and forearm fractures, and allows pinning of the fractured site under fluoroscopy for wrist and forearm fractures. The forearm and wrist fracture table 100 is applicable for all age groups so that the length and height of the device can be adjusted depending on the age. The forearm and wrist fracture table 100 can shorten surgery duration, enhance surgeon control on operation position especially during pinning, and a variable tensile force can be applied on fractured limbs during reduction and fixation.

Figure 2:
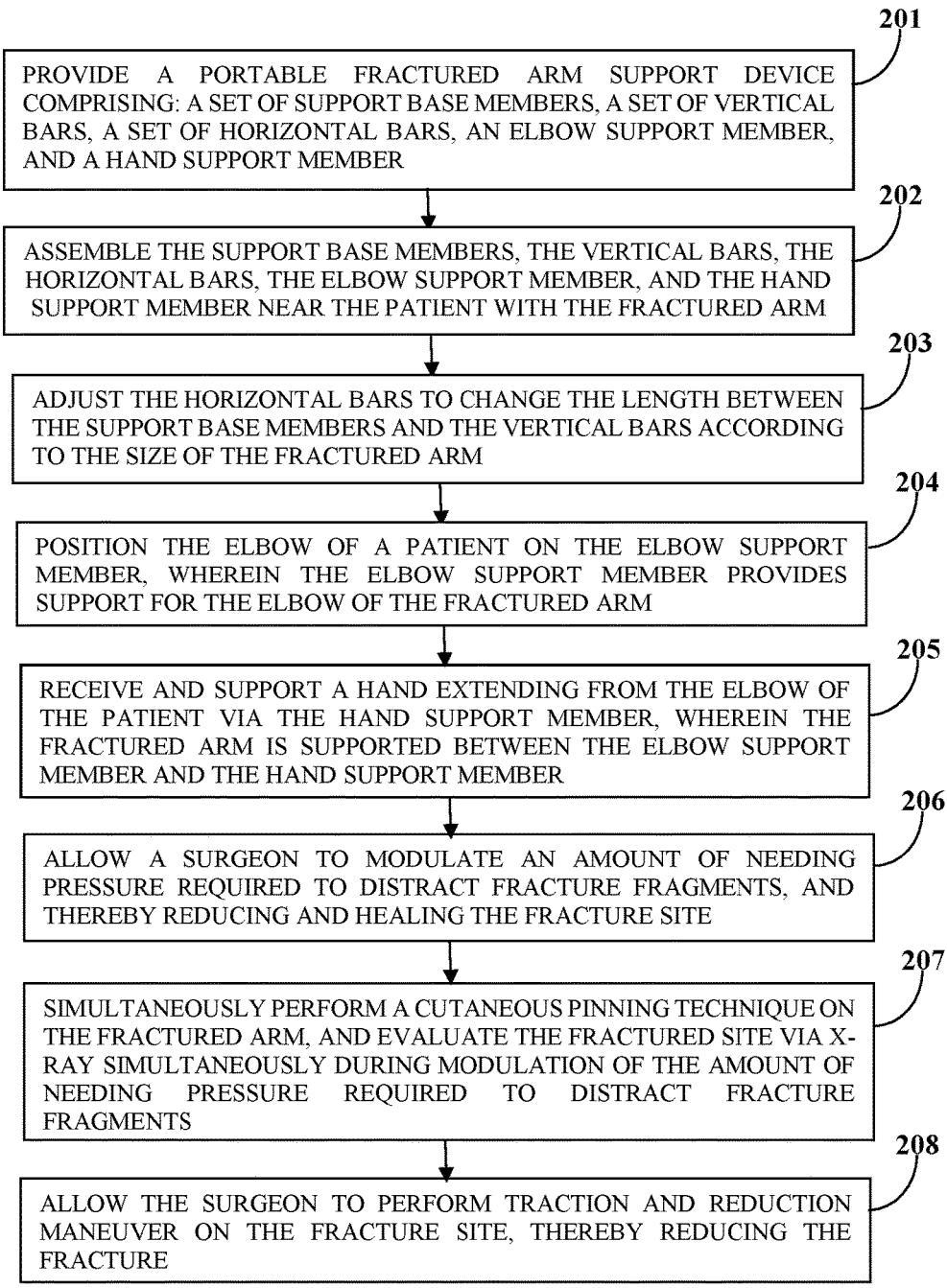
FIG. 2 exemplarily illustrates a method for supporting a fractured arm of a patient using the forearm and wrist fracture table.

FIG. 2 exemplarily illustrates a method for supporting a fractured arm 300 of a patient using the forearm and wrist fracture table 100. A method for supporting a fractured arm 300 of a patient is disclosed herein. The portable forearm and wrist fracture table 100 comprising a set of support base members 101, a set of vertical bars 102, a set of horizontal bars 105, an elbow support member 106, and a hand support member 108 is provided 201. The vertical bars 102 comprise a first vertical bar 103 and a second vertical bar 104 removably attached on upper surfaces of each of the support base members 101, and the horizontal bars 105 are removably attached between the support base members 101 and the vertical bars 102, where the horizontal bars 105 are configured to provide horizontal stability. The elbow support member 106 is defined by a cylindrical member 107 removably attached on an upper section 103a of the first vertical bar 103, and the hand support member 108 is defined by a curved plate member 109 removably attached to an upper section 104a of the second vertical bar 104.

A surgeon or a user assembles 202 the support base members 101, the vertical bars 102, the horizontal bars 105, the elbow support member 106, and the hand support member 108 near the patient with the fractured arm, and adjusts 203 the horizontal bars 105 to change the length between the support base members 101 and the vertical bars 102 according to the size of the fractured arm. The portable forearm and wrist fracture table 100 is transported and assembled near the patient itself in a condition where the patient is unable to move from the location of the accident.

Then the surgeon positions 204 the elbow of a patient on the elbow support member 106, where the elbow support member 106 provides support for the elbow of the fractured arm 300. As an example, the patient is allowed to encircle the elbow support member 106 with the bend created at the elbow, and therefore it enables the patient to extend the hand forward from the elbow support member 106 towards the next support component which is configured to support the hand of the patient.

The hand support member 108 receives and supports 205 a hand extending from the elbow of the patient, where the fractured arm 300 is supported between the elbow support member 106 and the hand support member 108. In an example, the hand support member 108 is flat in geometry and has a gripping surface which enables the hand of the patient to grip firmly the surface of the hand support member 108.

The forearm and wrist fracture table 100 allows 206 a surgeon to modulate an amount of needing pressure required to distract fracture fragments which reduces and heals the fracture site. One important technique is the cutaneous pinning technique or the percutaneous pinning which is used by orthopedic surgeons for steadying of uneven fractures. The method for supporting a fractured arm further comprises simultaneously allowing a surgeon or user to perform 207 a cutaneous pinning technique on the fractured arm 300, and evaluating the fractured site via x-ray. This step can be done after or during the step where the surgeon or user modulates the amount of needing pressure required to distract fracture fragments. For the final step of the method for supporting a fractured arm 208, the surgeon or user performs a traction and reduction maneuver on the fracture site, thereby reducing the fracture. The forearm and wrist fracture table 100 allows a surgeon to perform multiple activities at the same time during the examination or surgery of the fractured site of the patient.

Conventionally, most forms of fractures are operated into acceptable positions, restrained in a suitable cast, and are permitted to heal. But, in some cases, some kind of fractures cannot be steadied in an acceptable position by the aforementioned conventional method, and therefore necessitate some supplementary method of treatment which is known as percutaneous pinning. The pinning technique comprises the management, with an X-ray supervision, of the fracture into a satisfactory configuration, and the instant insertion of metallic pins, also known as Kirschner wires, through the skin into one of the bone fragments and across the fracture line into the other bone fragment.

Such pins are generally left in the designated position for a time period, for example, about four to six weeks, and are detached when the fracture has healed. The forearm and wrist fracture table 100 is used in this cutaneous pinning technique since the procedure requires the fractured site to be maintained at absolute rest where a doctor can easily operate around the fractured site to insert the pins and keep the fractured arm in the rest position for further recovery.

Now the forearm and wrist fracture table 100 is used further for setting of the fractures, also known in the art as fracture reduction, which necessitates the use of traction to the fractured arm or limb and the manipulation of the fragments which resulted during the fracture of the bone segment. This is done under x-ray supervision in order to align the structure of the bone in the natural form. In case of fractures that occurred to the longer bones in the arms, due to the incredible forces employed by the muscles on the bone, reduction of the fractured bone frequently necessitates maneuvering of the fragments with similar or larger counter acting forces applied by the surgeon and the other supporting medical personnel at numerous positions of the fractured arm.

The forearm and wrist fracture table 100 also finds great application after the surgery where it is usually essential to restrain the healing fractured arm in a considerably immobile, and raised position. In conventional systems, a metallic arm support assembly has been used in combination with a cast made of plaster to restrain a recovering fractured arm. The patient's fractured arm is therefore constrained in a configuration where he/she is practically unable to move the arm which is ultimately a result of such a configuration, owing to the inflexibility of the metallic frame assembly. Further, the weight of the metallic frame assembly makes motion of the arm almost impossible for the patient. In contrast to these conventional methods, in the case of the forearm and wrist fracture table 100, since most of the components are made of plastic, the weight of the overall device is considerably less as compared to the conventional metallic assemblies, and therefore allows a reasonable free movement of the patients' recuperating arm. This also allows for ease of portability and quick assembly at the site of patient's emergency.

Further, in some cases, considering the condition of the patient, it might be necessary to support the wrist and to permit active therapy of the hand. The conventional support devices do not offer satisfactory wrist support, or permit active therapy of the hand, thereby increasing the danger of numerous problems to the hand and the wrist. In addition, other conventional hand support devices have involved straps, one of which ranges from the anterior side of the support member and around the patient's neck to the posterior end of the support member, and the other of which ranges around the waist. Even though this assembly helps for easy manipulation of the arm as compared to the forearm and wrist fracture table 100, this assembly tends to apply stress to the patient's neck and has revealed to induce considerable uneasiness and tiredness. In addition, this assembly has also been shown to induce considerable distress to the patient when changing from an erect to a horizontal position.

However, the light weight forearm and wrist fracture table 100 offers support for the hands, wrist, as well as the elbow and reduces the uneasiness for the patient to move from erect to a horizontal position. The fractured recuperating arm is held in a better and more stable position on the forearm and wrist fracture table 100 as compared to the positioning on the conventional strap based devices.

Figure 3:
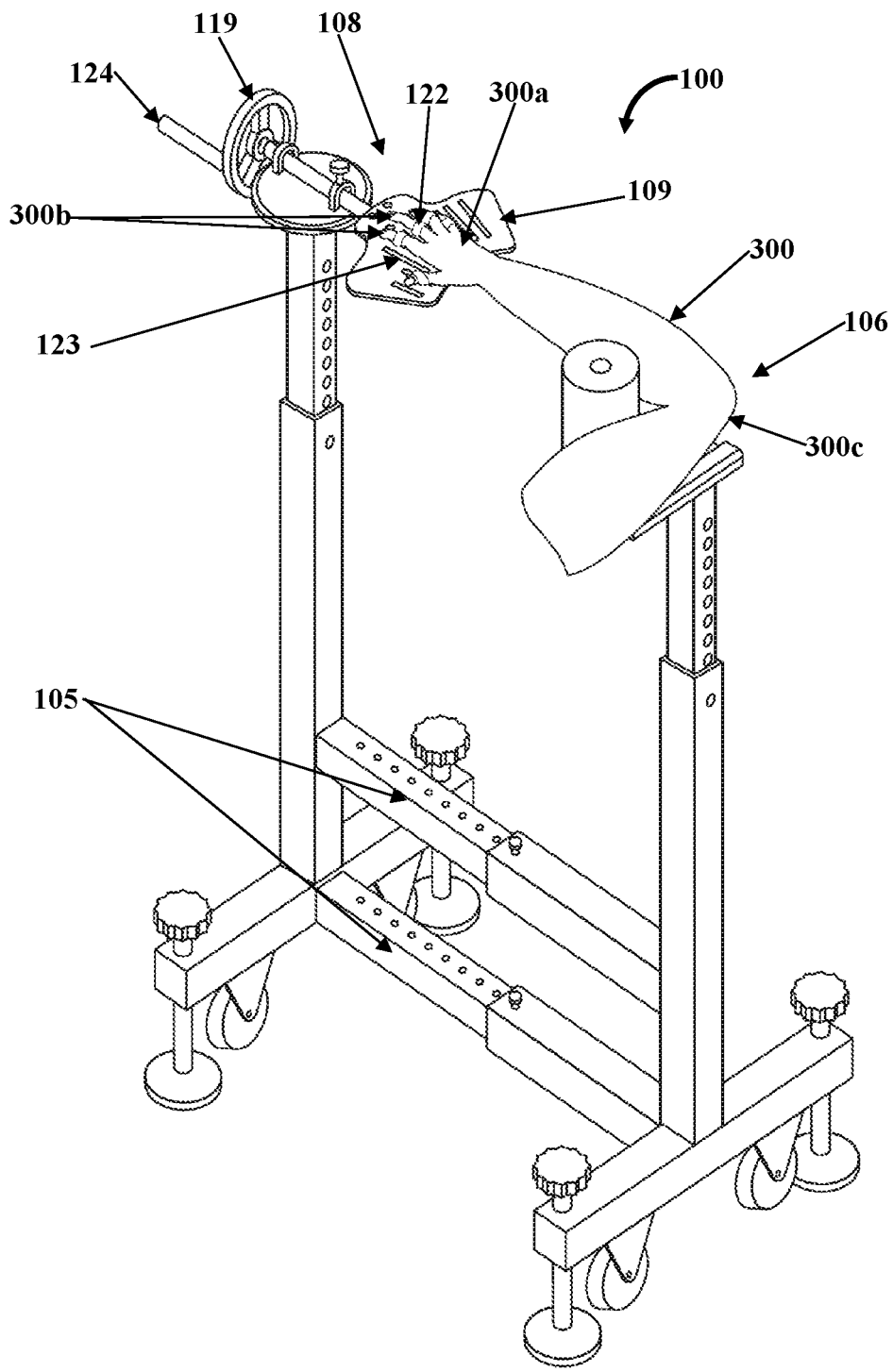
FIG. 3 exemplarily illustrates a front perspective view of a forearm and wrist fracture table, showing a fractured arm of a patient positioned between the elbow support member and the hand support member.

FIG. 3 exemplarily illustrates a front perspective view of a forearm and wrist fracture table 100, showing a fractured arm 300 of a patient positioned between the elbow support member 106 and the hand support member 108. As shown in FIG. 3, the patient's hand 300a or upper extremity is positioned on the forearm and wrist fracture table 100, while the forearm and wrist fracture table 100 can be located beside the bed of the patient.

In one example, the fingers 300b, or the distal part of the fractured arm 300, of the of the hand 300a of a patient are secured to the curved plate member 109 by fastening the fingers 300b to the curved plate member 109 using a strap member 122 which is configured to be looped through openings 123 positioned on the curved plate member 109, where the strap member 122 is looped through the openings 123 and between gaps of the fingers. Meanwhile the elbow 300c or the proximal section is configured to rest on the elbow support member 106, therefore the surgeon can operate an area of the fractured arm 300.

The length of the forearm and wrist fracture table 100 can be modulated in two different ways. For example, the horizontal bars 105 can be adjusted to change the distance between the elbow support member 106 and the hand support member 108 to facilitate a coarse tuning (see FIG. 3), where the traction generated by the coarse tuning allows the surgeon to maintain a longitudinal alignment of the fracture site and for him/her to evaluate the fracture under fluoroscopy. In another example, the fastening wheel 119 further comprises a handle 124 configured to rotate the fastening wheel 119. By rotating fastening wheel 119, one can fine tune and adjust the fracture site; where a clockwise turning of the handle 124 increases the traction in the fracture site, and counter-clock turning of the handle 124 relaxes traction in the fracture site.

So for the first part of traction, after fixing the upper extremity securely on this forearm and wrist fracture table 100, primary traction can be done by adjusting the horizontal bars 105, or the lower bar adjustment, and then the second part of the traction can be done by using the distal handle 124. During these processes, fracture reduction including fracture alignment in anterior-posterior and lateral views can be constantly checked by fluoroscopy and at the same time the surgeon can manipulate the fracture site by gentle manual force in different directions. In an example, as shown in FIG. 3, there is enough space in the lower side of the upper extremity to allow for the use of fluoroscopy during the fracture reduction procedure. When the surgeon is satisfied with the fracture reduction and alignment, the fracture would then be ready to fix by percutaneous pinning.

One aspect of the present disclosure is directed to a forearm and wrist fracture table configured to support a fractured arm of a patient during a medical procedure in order to rectify a fracture site of the fractured arm. The forearm and wrist fracture table comprises a set of support base members; a set of vertical bars that includes a first vertical bar and a second vertical bar that can be removably attached on upper surfaces of each of the support base members. The forearm and wrist fracture table further includes a set of horizontal bars which can be removably attached between the support base members and the vertical bars. These horizontal bars are configured to provide horizontal stability and can provide for length adjustment between the support base members and the vertical bars according to the size of the fractured arm.

The forearm and wrist fracture table further comprises an elbow support member defined by a cylindrical member that can be removably attached on an upper section of the first vertical bar. The elbow support member can provide support for the elbow of the fractured arm. The forearm and wrist fracture table further comprises a hand support member. This hand support member can be a curved plate member that can be removably attached to an upper section of the second vertical bar. The hand support member can be configured to receive and support a hand extending from the elbow of the patient, such that the fractured arm is supported between the elbow support member and the hand support member. Moreover, the support device allows for the needing pressure to be modulated and adjusted as required to distract fracture fragments, and thereby allows for better reduction and healing of the fractured site.

The set of support base members may comprise leg members that are fixedly attached proximal to opposing ends of a rod member. These leg members may be configured to contact the ground surface, thereby providing support. The leg members may have a screw jack assembly where a lead screw is adjusted via a gripper wheel which changes the height of the support base members from the ground level.

Each of the vertical bars may comprise concentric rectangular pipes sliding over each other, such that a plurality of holes are positioned on an inner pipe, and a hole positioned on an outer pipe through which a pin is introduced which selectively adjusts the length of the vertical bars. Similarly, each of the horizontal bars may comprise concentric rectangular pipes sliding over each other, wherein a plurality of holes are positioned on an inner pipe, and a hole positioned on an outer pipe through which a pin is introduced which selectively adjusts the length of the horizontal bars.

The elbow support member can be defined by the cylindrical member and may be positioned above a plate section. The hand support member may comprise the curved plate member fixedly attached at the distal end of a rod member. This distal end of the rod member can be threadably adjusted via a fastening wheel positioned at the opposing end of the rod member. The fastening wheel is able to adjust the length of the curved plate member according to the length of the fractured arm. The support device may be portable, in that many of the parts such as the support base members, the vertical bars, the horizontal bars, the elbow support member, and the hand support member are configured to be carried separately. This is one of the several advantages of the presently disclosed invention because for patients who are immobile and unable to move, this portable device allows for easy and quick assembly near the patient with the fractured arm especially under circumstances where the patient is unable to move.

In one example, this fracture support device may be in kit form, such that this portable, self-assembled device can easily be sent to hospitals or medical clinics at different locations with ease. The device can be easily assembled at the site of use in order to use the functionally advantageous features of this invention at remote locations.

The arm support device may be configured to allow the operator to perform a cutaneous pinning technique on the fractured arm. Moreover, the arm support device may also be configured to allow for the evaluation of the fractured site by permitting the simultaneous capture of x-rays of the arm and for the adjusting of the amount of needing pressure required to distract fracture fragments.

The arm support device is capable of traction and reduction maneuvers on the fracture site, thereby reducing the fracture. The arm support device may be configured to allow surgeons to perform intraoperative imaging of wrist and forearm fractures, and for the pinning of fractured sites under fluoroscopy for wrist and forearm fractures. The arm support device is also configured to enhance the surgeon's control on the operation position during pinning, and thereby can shorten the duration of surgery.

Figure 4:
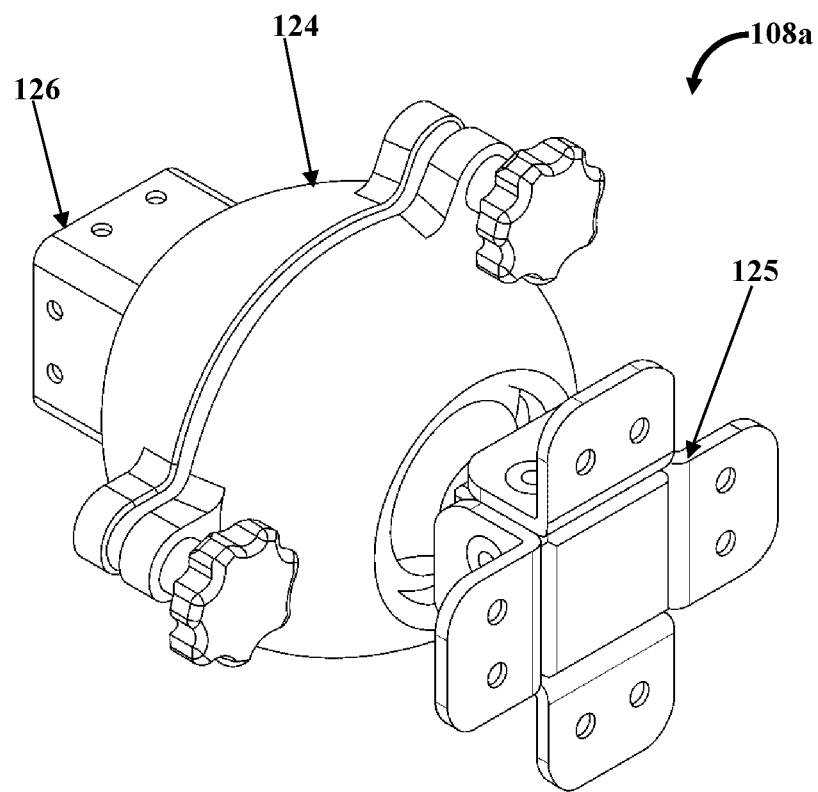
FIG. 4 exemplarily illustrates a side perspective view of another hand support member of the forearm and wrist fracture table.

FIG. 4 exemplarily illustrates a side perspective view of another hand support member 108a of the forearm and wrist fracture table 100. In an embodiment, the forearm and wrist fracture table 100 further comprises another hand support member 108a configured to position the fractured arm 300 as shown in FIG. 3, of the patient during per cutaneous pin fixation to treat distal radius fracture of the fractured arm 300. In general, distal radius fracture is one of the hardest fracture to treat because it mainly occurs in elderly people who have osteoporotic bone. For achieving a good result for treating the fracture, the orthopedic surgeon needs to be sure that he/she not only reduces the fracture properly, but also to correctly position the wrist/hand during the process of per cutaneous pin fixation. Further, the preferred position where such distal radius fracture can be secured properly is mild flexion and ulnar deviation of the wrist. To achieve this position after fracture reduction, another hand support member is therefore added to the fractured arm support device. This has the added feature of being able to permit the surgeon to perform different maneuvers at the fracture site which primarily includes wrist flexion and ulnar deviation.

After reduction of the fracture, the fractured arm 300 is secured by positioning the wrist for the mild flexion and ulnar deviation. This is checked with the C-ram, whereby the orthopedic surgeon is ready to fix the fracture with per cutaneous pinning. The hand support member 108a is attachable to the upper section 104a of the second vertical bar 104, as shown in FIG. 1, along the attachable base 126. The hand support member 108a comprises a rotatable sphere 127 as disclosed in the FIG. 5, pivotally disposed within a spherical shell 124. A portion of the rotatable sphere 127 is configured to fixedly attach a hand holding rib 125, where the patient is allowed to position the fractured arm 300 over any hand support device fastened over the hand holding rib 125 to perform one or combination of wrist flexion and ulnar deviation.

Figure 5:
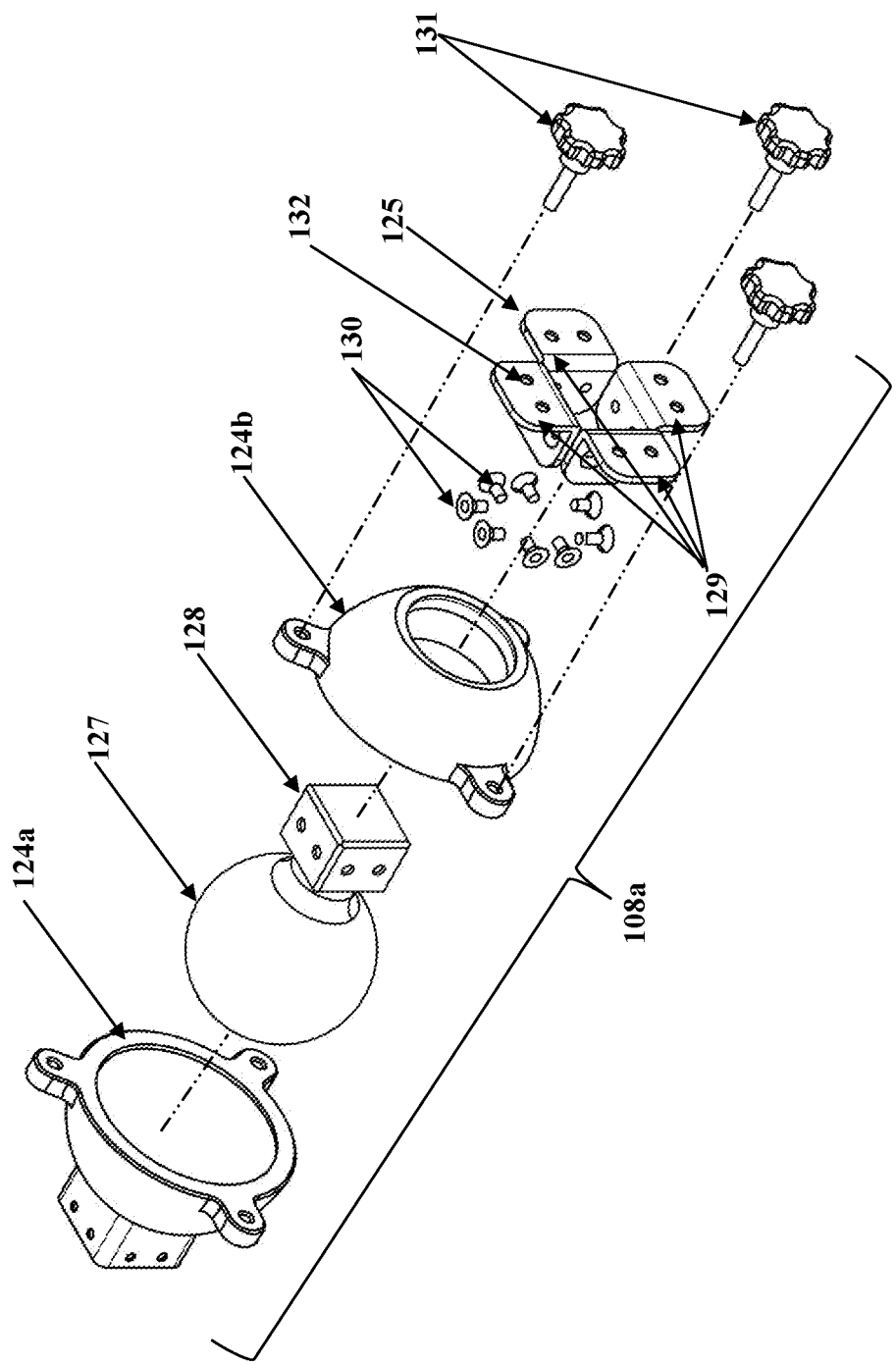
FIG. 5 exemplarily illustrates an exploded view of the hand support member disclosed in FIG. 4.

FIG. 5 exemplarily illustrates an exploded view of the hand support member 108a disclosed in FIG. 4. In an embodiment, the hand support member 108a disclosed here further comprises a first hemi-spherical shell 124a and a second hemi-spherical shell 124b which are fastened to each other via hand grippable screws 131 to define the spherical shell 124. The hand support member 108a also comprises a generally cube shaped support base member 128 positioned on the rotatable sphere 127 to fasten and support the hand holding rib 125 via fastener screws 130. The hand holding rib 125 comprises an assembly of four flanged plates 129 radially positioned with respect to each other, where each radially flanged plate 129 comprises fastener receiving holes 132 to receive and fasten one or more types of the hand support devices.

Another aspect of the present disclosure is directed to a forearm and wrist fracture table that is made of one or a combination of plastic and metal. The device is configured to support a fractured arm of a patient during a medical procedure to rectify a fracture site of the fractured arm. The device comprises a set of support base members, such that the set of support base members comprise leg members fixedly attached proximal to opposing ends of a rod member. The device further comprises a set of vertical bars comprising a first vertical bar and a second vertical bar removably attached on upper surfaces of each of the support base members; and a set of horizontal bars removably attached between the support base members and the vertical bars. These horizontal bars are configured to provide horizontal stability and length adjustment between the support base members and the vertical bars, according to the size of the fractured arm.

As disclosed in FIGS. 4 and 5, proceeding to the reduction of the fracture, a mild flexion and ulnar deviation check is performed on the fractured arm 300 by positioning the wrist on the fractured arm support device 100. The mild flexion and ulnar deviation is checked using a C-ram, where the orthopedic surgeon makes necessary decisions to fix the fracture with per cutaneous pinning, and any other similar technique. The hand support member 108a is removably attached to the upper section 104a of the second vertical bar 104, along the attachable base 126, as shown in FIG. 4. The rotatable sphere 127 as disclosed in the FIG. 5, is pivotally disposed within a spherical shell 124 which allows for the rotation of the wrists along a vertical axis of the hand support member 108a. A portion of the rotatable sphere 127 is configured to fixedly attach a hand holding rib 125, where the patient is allowed to position the fractured arm 300 over any hand support device fastened over the hand holding rib 125 to perform one or combination of wrist flexion and ulnar deviation.

Figure 6:
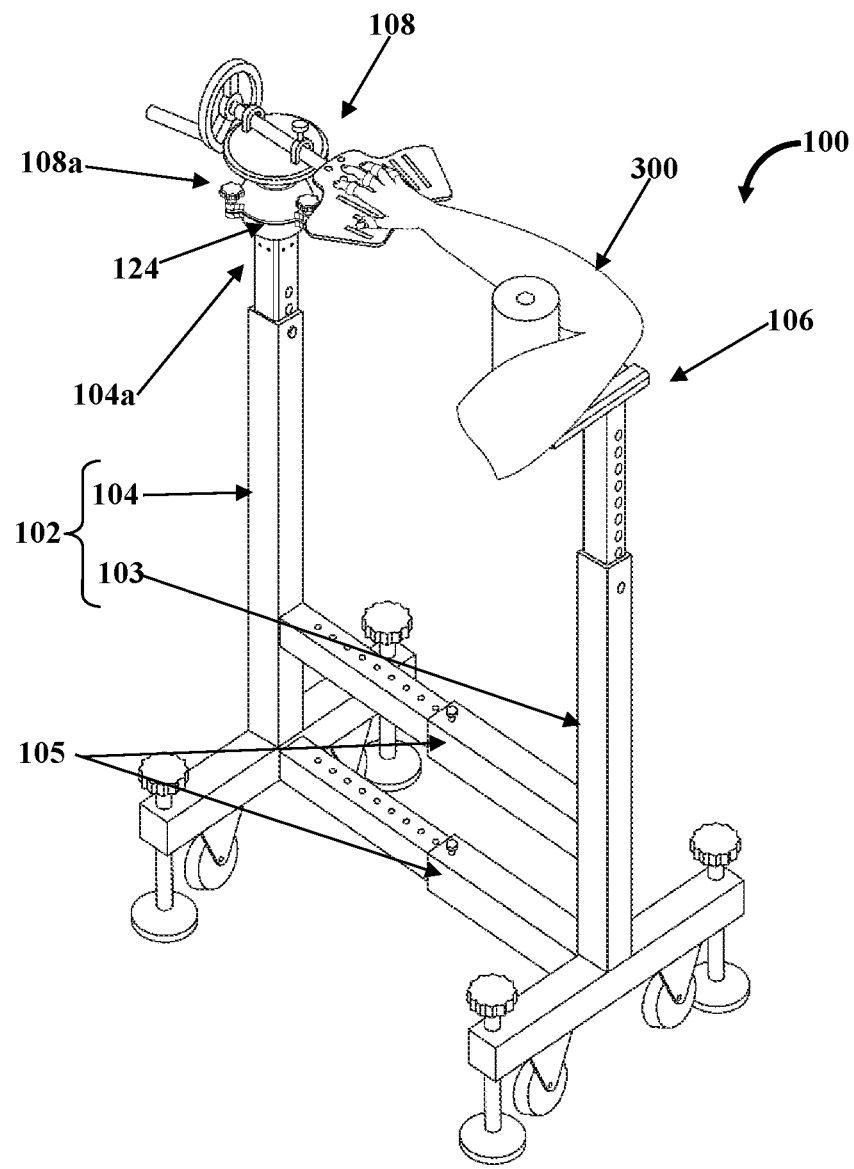
FIG. 6 exemplarily illustrates another front perspective view of a fractured arm support device, with the another hand support member disclosed in FIGS. 4 and 5.

FIG. 6 exemplarily illustrates another front perspective view of a fractured arm support device 100, with the another hand support member 108a disclosed in FIGS. 4 and 5. The spherical hand support member 108a is defined by the spherical shaped member is removably attached to an upper section 104a of the second vertical bar 104, wherein the spherical hand support member 108a is configured to receive and support a hand support member 108 which was disclosed in FIG. 1. Here, the fractured arm 300 is supported between the elbow support member 106 and the hand support member 108 which is rotatably connected to the spherical hand support member 108a. Now, in an initial stage, the surgeon is allowed to modulate an amount of needing pressure required to distract fracture fragments, and thereby reducing and healing the fracture site.

The forearm and wrist fracture table further comprises an elbow support member defined by a cylindrical member removably attached on an upper section of the first vertical bar. This elbow support member may be positioned above a plate section to provide support for the elbow of the fractured arm. The forearm and wrist fracture table further comprises a hand support member defined by a curved plate member removably attached to an upper section of the second vertical bar. This hand support member may comprise the curved plate member fixedly attached at the distal end of a rod member which is adjusted via a fastening wheel positioned at the opposing end of the rod member. The hand support member can be configured to receive and support a hand extending from the elbow of the patient, wherein the fractured arm is supported between the elbow support member and the hand support member. The arm support device may be configured to allow the operator to adjust the amount of needing pressure required to distract fracture fragments, thereby causing a reduction and promoting healing of the fracture site. Furthermore, the device may be configured to allow this adjusting of the needing pressure to be done simultaneously to performing a cutaneous pinning technique on the fractured arm and the concurrent evaluation of the fractured site via x-ray. The arm support device is capable of traction and reduction maneuvers on the fracture site, thereby reducing the fracture.

The leg members can be configured to contact the ground surface to provide support for the forearm and wrist fracture table. The fingers of the hand of a patient can be secured to the curved plate member by fastening the fingers to the curved plate member using a strap member. This strap member is configured to be looped through openings positioned on the curved plate member, such that the strap member is looped through the openings and between gaps of the fingers. The horizontal bars can be adjusted to change the distance between the elbow support member and the hand support member to facilitate a coarse tuning. In one example, the traction generated by the coarse tuning allows the surgeon to maintain longitudinal alignment of the fracture site and enables him/her to evaluate the nature and extent of the fracture under fluoroscopy.

In the teachings of the present disclosure, the fastening wheel adjusts the length of the curved plate member according to the length of the fractured arm. The fastening wheel further comprises a handle configured to rotate the fastening wheel, thereby allowing for the fine tuning with the fastening wheel to adjust the fracture site. For this fine tuning, a clockwise turning of the handle increases the traction in the fracture site, and a counter-clockwise turning of the handle relaxes traction in the fracture site.

The unique design of this device allows for the ability to securely fix proximal (elbow) and distal (fingers) part of the area that may be operated on. The length of device can be modulated in two different ways. First by changing length of the bar that attaches lower part of the device (coarse tuning): this traction allows the surgeon to maintain the longitudinal alignment of the fracture site and to evaluate the nature and extent of the fracture under fluoroscopy. Second, by using the handle that is located at the distal part of the device (fine tuning). As outlined above, the clockwise turning increases the traction in the fracture site and counter-clockwise turning relaxes traction. Thus, for the first part of traction, after fixing the upper extremity securely on this device, primary traction could be done by lower bar adjustment and then second part of traction could be done by using the distal handle.

Another aspect of the present disclosure is directed to a method for supporting a fractured arm of a patient. This method comprises providing a portable forearm and wrist fracture table comprising: a set of support base members; a set of vertical bars comprising a first vertical bar and a second vertical bar removably attached on upper surfaces of each of the support base members; a set of horizontal bars removably attached between the support base members and the vertical bars, wherein the horizontal bars are configured to provide horizontal stability; an elbow support member defined by a cylindrical member removably attached on an upper section of the first vertical bar; and a hand support member defined by a curved plate member removably attached to an upper section of the second vertical bar.

The method for supporting a fractured arm of a patient further comprises assembling the support base members, the vertical bars, the horizontal bars, the elbow support member, and the hand support member near the patient with the fractured arm; and adjusting the horizontal bars to change the length between the support base members and the vertical bars according to the size of the fractured arm. The method further comprises positioning the elbow of a patient on the elbow support member, such that the elbow support member provides support for the elbow of the fractured arm. Moreover, the method comprises receiving and supporting a hand extending from the elbow of the patient via the hand support member, such that the fractured arm is supported between the elbow support member and the hand support member; and allowing a surgeon to modulate an amount of needing pressure required to distract fracture fragments in order to reduce and heal the fracture site.

The method for supporting a fractured arm of a patient further comprises simultaneously performing a cutaneous pinning technique on the fractured arm, and evaluating the fractured site via x-ray. This capability of performing pinning and simultaneously being able to perform x-rays is very valuable and provides for easier and real-time effective evaluation of the fracture by the surgeon. Moreover, this can also be done during modulation of the amount of needing pressure required to distract fracture fragments. Lastly, the method for supporting a fractured arm further comprises allowing the surgeon to perform traction and reduction maneuver on the fracture site, thereby reducing the fracture. The presently taught method may further comprise performing intraoperative imaging of wrist and forearm fractures, and pinning of the fractured site under fluoroscopy for wrist and/or forearm fractures.

One aspect of the present disclosure is directed to a forearm and wrist fracture table. The device comprises a set of support base members, wherein the set of support base members comprise leg members fixedly attached proximal to opposing ends of a rod member; a set of vertical bars comprising a first vertical bar and a second vertical bar removably attached on upper surfaces of each of the support base members; and a set of horizontal bars removably attached between the support base members and the vertical bars, wherein the horizontal bars are configured to provide horizontal stability and length adjustment between the support base members and the vertical bars according to the size of the fractured arm. The device further comprises an elbow support member defined by a cylindrical member removably attached on an upper section of the first vertical bar, wherein the elbow support member is positioned above a plate section to provide support for the elbow of the fractured arm; and a hand support member defined by a curved plate member removably attached to an upper section of the second vertical bar.

The hand support member may comprise the curved plate member fixedly attached at the distal end of a rod member which is adjusted via a fastening wheel positioned at the opposing end of the rod member. The hand support member may be configured to receive and support a hand extending from the elbow of the patient. The fractured arm can be supported between the elbow support member and the hand support member. The arm support device may be configured to allow the operator to adjust the amount of needing pressure required to distract fracture fragments, thereby causing a reduction and promoting healing of the fracture site. The device may be configured to allow this adjusting of the needing pressure to be done simultaneously to performing a cutaneous pinning technique on the fractured arm.

Moreover, the arm support device may be capable of traction and reduction maneuvers on the fracture site. The fastening wheel may further comprise a handle configured to rotate the fastening wheel to allow for the fine tuning with the fastening wheel to adjust the length of the curved plate member according to the length of the fractured arm. A clockwise turning of the handle of the fastening wheel can increases the traction in the fracture site, and counter-clock turning of the handle can relax traction in the fracture site.

Each of the vertical bars may comprise concentric rectangular pipes sliding over each other, such that a plurality of holes are positioned on an inner pipe, and a hole positioned on an outer pipe through which a pin is introduced which selectively adjusts the length of the vertical bars. Similarly, each of the horizontal bars may comprise concentric rectangular pipes sliding over each other, wherein a plurality of holes are positioned on an inner pipe, and a hole positioned on an outer pipe through which a pin is introduced which selectively adjusts the length of the horizontal bars.

In one embodiment, the forearm and wrist fracture table further comprising another hand support member configured to position the fractured arm of the patient during per cutaneous pin fixation to treat distal radius fracture of the fractured arm, wherein the hand support member comprises a rotatable sphere pivotally disposed within a spherical shell, wherein a portion of the rotatable sphere is configured to fixedly attach a hand holding rib, wherein the patient is allowed to position the fractured arm over any hand support device fastened over the hand holding rib to perform one or combination of wrist flexion and ulnar deviation.

In one example, the hand support member further comprises; a first hemi-spherical shell and a second hemi-spherical shell fastened to each other to define the spherical shell; and a generally cube shaped support base member positioned on the rotatable sphere to fasten and support the hand holding rib, wherein the hand holding rib comprises an assembly of four flanged plates radially positioned with respect to each other, wherein each radially flanged plate comprises fastener receiving holes to receive and fasten one or more types of the hand support devices.

The foregoing examples have been provided merely for the purpose of explanation and are in no way to be construed as limiting of the present concept disclosed herein. While the concept has been described with reference to various embodiments, it is understood that the words, which have been used herein, are words of description and illustration, rather than words of limitation. Further, although the concept has been described herein with reference to particular means, materials, and embodiments, the concept is not intended to be limited to the particulars disclosed herein; rather, the concept extends to all functionally equivalent structures, methods and uses, such as are within the scope of the appended claims. Those skilled in the art, having the benefit of the teachings of this specification, may affect numerous modifications thereto and changes may be made without departing from the scope and spirit of the concept in its aspects.

The invention claimed is:

1. A forearm and wrist fracture table, comprising:
a set of support base members, wherein the set of support base members comprise leg members fixedly attached proximal to opposing ends of a bar member;
a set of vertical bars comprising a first vertical bar and a second vertical bar removably attached on upper surfaces of each of the set of support base members;
a set of horizontal bars removably attached between the set of support base members and the set of vertical bars, wherein the horizontal bars are configured to provide horizontal stability and length adjustment between the set of support base members and the set of vertical bars;
an elbow support member defined by a cylindrical member removably attached on an upper section of the first vertical bar, wherein the elbow support member is positioned above a plate section to provide support for the elbow of the fractured arm;

a hand support member defined by a curved plate member removably attached to an upper section of the second vertical bar, wherein the hand support member comprises the curved plate member fixedly attached at the distal end of a rod member which is adjusted via a fastening wheel positioned at the opposing end of the rod member, wherein the hand support member is configured to receive and support a hand extending from the elbow of the patient, wherein the fractured arm is capable of being supported between the elbow support member and the hand support member, wherein the forearm and wrist fracture table is configured to allow the operator to adjust the amount of needing pressure required to distract fracture fragments, thereby causing a reduction and promoting healing of the fractured site of the fractured arm, and wherein the forearm and wrist fracture table is configured to allow this adjusting of the needing pressure to be done simultaneously to performing a cutaneous pinning technique on the fractured arm, wherein forearm and wrist fracture table is capable of traction and reduction maneuvers on the fracture site, and wherein the fastening wheel further comprises a handle configured to rotate the fastening wheel to allow for the fine tuning with the fastening wheel to adjust the length of the curved plate member, wherein a clockwise turning of the handle increases the traction in the fracture site, and counter-clock turning of the handle relaxes traction in the fracture site.

2. The forearm and wrist fracture table of claim 1, wherein each of the set of vertical bars comprises concentric rectangular pipes sliding over each other, wherein a plurality of holes are positioned on an inner pipe, and a hole positioned on an outer pipe through which a pin is introduced which selectively adjusts the length of each vertical bar of the set of vertical bars; and wherein each of the set of horizontal bars comprises concentric rectangular pipes sliding over each other, wherein a plurality of holes are positioned on an inner pipe, and a hole positioned on an outer pipe through which a pin is introduced which selectively adjusts the length of each horizontal bar of the set of horizontal bars.

3. The forearm and wrist fracture table of claim 1, further comprising the hand support member configured to position the fractured arm of the patient during per cutaneous pin fixation to treat distal radius fracture of the fractured arm, wherein the hand support member comprises a rotatable sphere pivotally disposed within a spherical shell, wherein a portion of the rotatable sphere is configured to fixedly attach a hand holding rib, wherein the patient is allowed to position the fractured arm over the hand support member fastened over the hand holding rib to perform one or combination of wrist flexion and ulnar deviation.

4. The forearm and wrist fracture table of claim 3, wherein the hand support member of claim 3 further comprises; a first hemi-spherical shell and a second hemi-spherical shell fastened to each other to define the spherical shell; and a generally cube shaped support base member positioned on the rotatable sphere to fasten and support the hand holding rib, wherein the hand holding rib comprises an assembly of four flanged plates radially positioned with respect to each other, wherein each radially flanged plate comprises fastener receiving holes to receive and fasten the hand support member.

* * * * *